Feb. 6, 1973 J. F. GRAHAM Re 27,571

SURGICAL DRESSING

Filed Nov. 18, 1968

Inventor.
James F. Graham.
By Hume, Clement, Hume & Lee
Attys.

United States Patent Office

Re. 27,571
Reissued Feb. 6, 1973

27,571
SURGICAL DRESSING

James F. Graham, 9760 S. Kedzee Ave.,
Evergreen Park, Ill. 60642

Original No. 3,521,632, dated July 28, 1970, Ser. No. 776,340, Nov. 18, 1968. Application for reissue July 1, 1971, Ser. No. 159,073
Int. Cl. A61l *15/00*
U.S. Cl. 128—156 14 Claims

Matter enclosed in heavy brackets [ ] appears in the original patent but forms no part of this reissue specification; matter printed in italics indicates the additions made by reissue.

ABSTRACT OF THE DISCLOSURE

A surgical dressing which is adjustable for size and shape. An inner lining of non-adhering fluid-permeable fabric is roughly shaped to conform to the human trunk. A congruent mass of fluid-absorbent material is superimposed on the inner lining, and covered with an outer lining of moisture-resistant fabric. All three layers are fastened together about their contiguous edges with a fabric tape. A plurality of spaced lines of stitching are provided through the outer lining and the mass of absorbent material. The stitching lines permit cutting of the dressing to size and shape without disturbing the structural integrity of the absorbent mass.

BACKGROUND—SUMMARY—DRAWINGS

This invention relates to a surgical dressing and, more particularly, to a dressing which is adjustable for size and shape by cutting.

U.S. Pat. No. 3,343,537, which issued to the present applicant on Sept. 26, 1967, discloses a novel type of surgical dressing having certain unique characteristics. That dressing includes an inner or skin-side lining of lightweight, non-adhering fabric which is permeable to fluids. Fastened to the inner lining is a congruent mass of absorbent material, such as multiple layers of surgical gauze. The inner lining is fastened to the mass of gauze, in general, only about their common congruent edges. The layers of gauze themselves are stitched together only at certain locations in order to provide structural strength to the mass.

The inner lining, which is worn next to the skin and which covers the damaged tissues, permits the exudate from the damaged area to pass therethrough into the mass of absorbent material. In addition, the inner lining permits the passage of air to the wound, and provides a supporting structural framework for the formation of healing cellular tissue. Moreover, because of the non-adhering nature of the inner lining, it does not adhere or cause irritation to undamaged skin or tissues. The fact that the inner lining is connected to the mass of absorbent material only about their contiguous edges permits the sliding of the mass of absorbent material without consequent pulling of the inner lining and damage to the healing wound. Such dressings can be made in a variety of shapes and sizes, to conform to various anatomical contours of the human body.

It has now been found that, with certain important modifications to the basic dressing structure disclosed in the above described patent, an improved surgical dressing can be constructed which possesses certain useful advantages and which is more readily adaptable to use under a variety of circumstances and with a variety of wounds or injuries. In particular, it has been found that a surgical dressing may be provided which, although constructed as a single unit, may be readily adjusted for size and shape and, indeed, may be completely severed into smaller portions for use in connection with human extremities and the like. In addition, relatively cheap materials may be employed to adapt the improved dressing for use under adverse conditions, as for example for battlefield casualties or emergency use.

Accordingly, the improved surgical dressing of the present invention contemplates the use of an inner lining of flexible, non-adhering, fluid-permeable material, upon which is superimposed a mass of fluid-absorbent material, as in the above described U.S. Pat. No. 3,343,537. An outer protective lining may be provided over the mass of absorbent material, when the dressing is intended for use under emergency or battlefield conditions. This outer lining may be of relatively heavy moisture-resistant fabric or, when intended for use under less severe conditions, of paper which is preferably treated to resist moisture. In addition, there is provided a plurality of spaced lines of stitching through the mass of absorbent material and, if an outer lining is provided, through that outer lining as well. The stitch-lines are adapted to preserve the structural integrity of the absorbent material when the dressing is cut or partially severed. Thus, by appropriate placement of the stitch-lines, the dressing is made adjustable in size and shape, and may be made to fit any desired portion of any size body simply by cutting with a scissors or other suitable device. Indeed, by locating one or more longitudinal stitch-lines near the longitudinal center line of the dressing, it may be completely severed into two halves, which may then be adapted by further trimming to fit a body extremity. A further advantage of the improved dressing structure lies in the fact that the plurality of spaced stitch-lines and, where employed, the protective outer lining, permit the use of lower cost absorbent material, as for example paper and the like.

The foregoing and additional features and advantages of the present invention will be more fully understood by considering the remainder of the specification and the claims, with illustrative reference to the drawing, in which:

DETAILED DESCRIPTION OF EXEMPLARY EMBODIMENT

Figure 1:
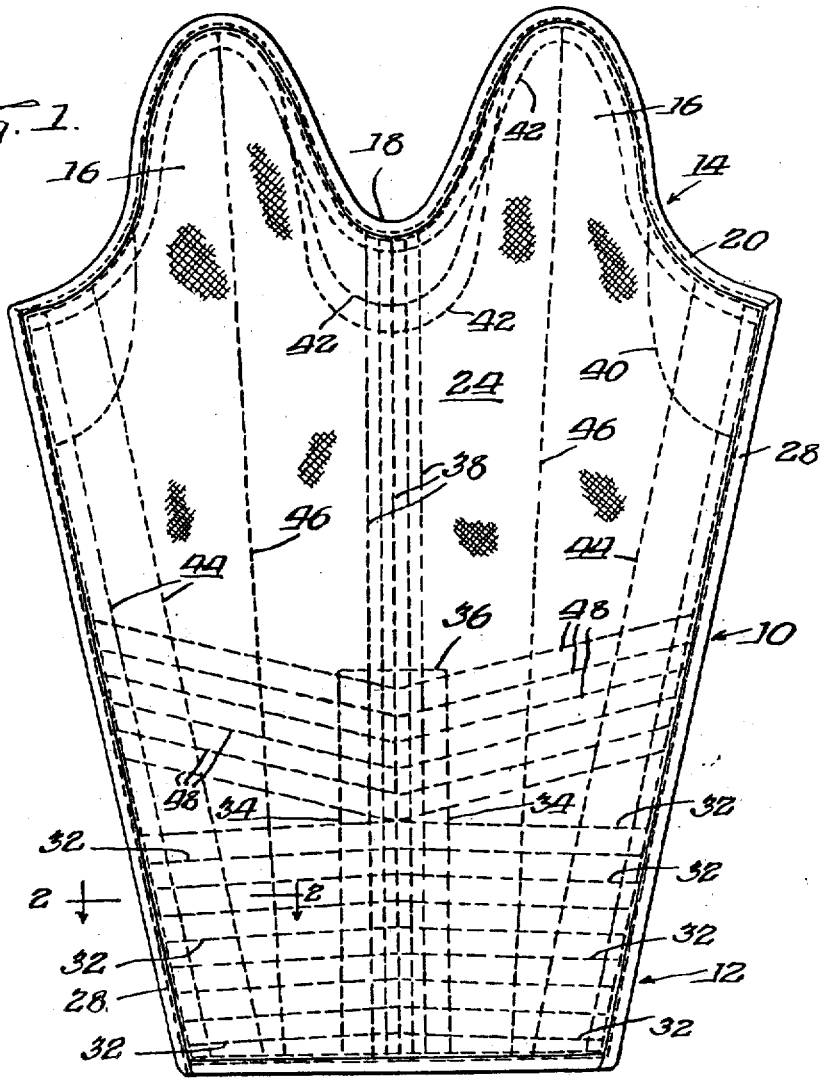
FIG. 1 is a plan view of a surgical dressing constructed in accordance with the invention.

With reference to the drawing, there is shown a surgical dressing 10 constructed in accordance with the present invention. As illustrated in FIG. 1, the dressing 10 is generally shaped to conform roughly to the contour of a human trunk. Thus, the dressing 10 includes a lower portion 12 adapted for contact with the lower portion of the trunk and the lower extremities, and an upper portion 14 adapted for contact with the upper portion of the trunk and the shoulders. The upper portion 14 includes a pair of shoulder-covering extensions 16 which define a central neck-encircling area or opening 18. The shoulder extensions 16 curve downwardly toward the edges of the dressing 10 to define armpit-encircling portions or depressions 20.

Figure 2:
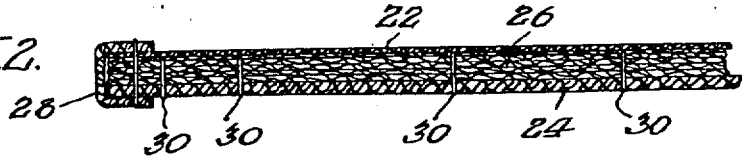
FIG. 2 is a cross-sectional view of a portion of the dressing, taken on the line 2—2 of FIG. 1.

As best seen in FIG. 2, the dressing 10 formed of an inner, or skin-side lining 22 and an outer lining 24. The space between the two linings 22 and 24 is filled with a mass of material 26. All three of the components 22, 24 and 26 are fastened together at their contiguous edges by means of a tape 28. The inner and outer linings 22 and 24 and the material 26 are essentially congruent in shape, and the fastening tape 28 runs around the entire periphery of the dressing 10. As illustrated in FIG. 1, the outer lining 24 is uppermost in the plan view shown there.

The inner lining 22 may be made of any suitable fabric or equivalent flexible material which is characterized by being non-adhering and fluid-permeable. The non-adhering characteristic of inner lining 22 is principally intended to prevent the lining from sticking or adhering to undamaged portions of skin and tissue surrounding a wound or burn. The fluid-permeable characteristic of the lining 22 is intended to permit the passage therethrough of body fluids or exudate from the burn or wound which the dressing 10 is used to cover. Many relatively light-weight fabrics having a slick finish will satisfy these requirements, as for example silk, rayon and the like. Other materials which have been found highly suitable for this purpose are the outer covering of "Dermicel" brand sterile pads, and the skin-side layer of "Microdin" brand dressings.

The outer lining 24 is in general intended to serve a protective function, and may be dispensed with entirely where the dressing 10 is intended for use only in a controlled environment, such as a hospital or clinic. However, where the dressing 10 is intended for use under adverse conditions, as for example in the battlefield or for emergency use, the outer lining 24 is preferably formed of a relatively heavy fabric such as cotton, which has been treated to resist moisture. It should be understood, however, that a dressing having an outer lining 24 of moisture-resistant fabric may also be used under less adverse conditions, as in a hospital. Alternatively, the outer lining 24 may be formed of less expensive materials, as for example paper which has been treated to resist moisture. In general, the provision of an outer lining 24 provides increased structural strength for the dressing 10, and in particular enhances the wearability of the intermediate mass of material 26.

Figure 3:
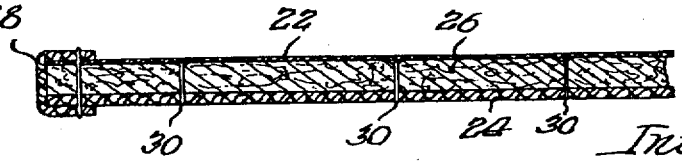
FIG. 3 is a view similar to that of FIG. 2, showing a modification of the dressing.

The mass of material 26, as shown in FIG. 2, comprises multiple layers of fluid-absorbent material, as for example cotton surgical gauze. Inasmuch as the principal function of the material 26 is to absorb body fluids or exudate which passes through the inner lining 22, the material should be chosen with an eye toward its ability to retain strength and still have the ability to absorb substantial amounts of fluid. In addition to surgical gauze, other materials which have proved satisfactory in this respect are masses of paper of the consistency and weight of ordinary facial tissues, and various types of cellulosic batting, as for example cotton batting. FIG. 3 illustrates a modified form of the dressing 10 wherein the intermediate material 26 comprises paper or cotton.

It will be noted particularly from inspection of FIGS. 2 and 3, that a plurality of lines of stitching 30 pass through the outer lining 24 and the absorbent material 26. These stitch-lines 30 do not pass through the inner lining 22. Preferably, the inner lining 22 is fastened to the outer lining 24 and the mass of material 26 only at the contiguous edges thereof by means of the tape 28. This constructional feature permits relative sliding between the inner lining 22 and the remainder of the dressing 10. Where the outer lining 24 is dispensed with, the stitch-lines 30 would pass only through the mass of absorbent material 26.

As best shown in FIG. 1, the dressing 10 includes a number of the lines of stitching 30 spaced at more or less regular intervals. Near the lower or bottom portion 12 of the dressing 10 is a group of stitch-lines 32 which run transversely across the dressing. The stitch-lines 32 provide means for adjustment of the dressing 10. Thus, if a severing cut is made, as for example through the three layers 22, 24 and 26 between a pair of stitch-lines 32 (or along but slightly outside of one of the stitch-lines 32), any selected lowermost portion of the dressing 10 may be removed without disturbing the integrity of the lining 24 and the mass of absorbent material 26. The presence of the last stitch-line 32 adjacent to the line of cut prevents disintegration of the absorbent material 26 and undue fraying or displacement of the outer lining 24 and the material 26.

A pair of spaced longitudinal stitch-lines 34, which are connected by a relatively short transverse stitch-line 36, define a generally rectangular crotch portion for the dressing 10. Thus, in order to permit perineal care or to facilitate fitting of the dressing to the lower extremities, cuts can be made along the inside of the rectangular boundary defined by the stitch-lines 34 and 36, and the entire crotch portion of the dressing 10 may be cut away. Alternatively, any of the transverse lines 32 might be used to form the upper boundary of the crotch portion.

The dressing 10 also includes a series of spaced longitudinal stitch-lines 38 which extend from the lower edge of the dressing to the neck opening 18. Cutting along any of the stitch-lines 38 will permit complete longitudinal severing of the entire dressing or, when it is desired to expose a portion of the body for examination or treatment, only partial longitudinal cuts may be made.

The dressing 10 also includes a group of generally arcuate stitch-lines 40 along which cuts may be made in order to enlarge the armholes 20. Similarly, the dressing includes a group of stitch-lines 42 which permit enlargement of the neck opening 18 and which might also be used to shorten the shoulder extensions 16.

Also included in the dressing 10 are a group of stitch-lines 44 which extend generally parallel to the sides of the dressing. Cutting along the stitch-lines 44 permits adjustment of the width of the dressing. The dressing 10 further includes a pair of longitudinal stitch-lines 46 which extend from the bottom portion 12 of the dressing to the center point of the shoulder extension 16. Again, complete or partial severing cuts may be made along the stitch-lines 46 to permit complete subdivision of the dressing or to permit examination or treatment of a portion of the body. Finally, the dressing 10 includes a series of generally parallel stitch-lines 48 extending in an oblique direction transversely across the dressing from the central longitudinal stitch-lines 38.

It will be apparent that, although the dressing 10 as illustrated in FIG. 1 is of a shape suitable for general conformity to the human trunk, almost any desired size or shape of dressing may be constructed by appropriate cutting along any of the stitch lines. For example, a dressing suitable for use in connection with a burn or wound on a small portion of one of the extremities could be made by simply cutting along one of the oblique stitch-lines 48 and one of the central longitudinal stitch-lines 38. As another example, a dressing suitable for contact with only the uppermost portion of the body might be constructed by cutting along two intersecting oblique stitch-lines 48.

As can be see from the foregoing, the present invention provides an improved surgical dressing which has the beneficial features of a non-adhering fluid-permeable inner lining, a protective outer lining, and an intermediate mass of fluid-absorbent material. Through the use of appropriately placed lines of stitching through the adsorbent material and the outer lining, the dressing is adjustable for nearly any desired size or shape, without destroying the structural integrity of the dressing. In addition, the stitch-lines permit any selected portion of the body which is covered thereby to be exposed for treatment or examination, again without destroying the structural integrity of the dressing.

Although an embodiment constructed in accordance with the present invention has been described with the requisite particularity, the disclosure is of course only exemplary. Consequently, numerous changes in details of construction, in size, configuration and arrangement of components and materials, and in modes of application will be apparent to those familiar with the art and may be resorted to without departing from the scope of the invention as set forth in the following claims.

I claim:

1. A surgical dressing adjustable for size and shape, comprising a flexible, non-adhering, fluid-permeable inner lining; a mass of fluid-absorbing material superposed congruently with said inner lining; means for fastening said inner lining and said mass together about their congruent peripheries; and a plurality of spaced lines of stitching through said mass, said stitch-lines being adapted to maintain the structural integrity of said mass when a severing cut is made through said dressing adjacent one of said stitch-lines, said stitch-lines being positioned to permit selective adjustment of the size and shape of said dressing by cutting.

2. A dressing in accordance with claim 1, including a flexible outer lining superposed congruently with said mass, with said stitch-lines extending through said outer lining and said mass.

3. A dressing in accordance with claim 2, wherein said outer lining is a moisture-resistant fabric.

4. A dressing in accordance with claim 2, wherein said outer lining is paper.

5. A dressing in accordance with claim 1, wherein said mass consists of multiple layers of surgical gauze.

6. A dressing in accordance with claim 1, wherein said mass consists of paper.

7. A dressing in accordance with claim 1, wherein said mass consists of cellulose batting.

8. A surgical dressing adjustable for size and shape, comprising a non-adhering porous inner lining roughly shaped to be conformably wrapped about a human trunk; a mass of absorbent material superposed congruently with said inner lining; a protective outer lining superposed congruently with said mass; means for fastening said linings and said mass together about their congruent peripheries; and a plurality of spaced lines of stitching through said mass and said outer lining, at least one of said stitch-lines being located to permit adjustment of the length of said dressing.

9. A dressing in accordance with claim 8, wherein at least one of said stitch-lines is located to permit adjustment of the width of said dressing.

10. A dressing in accordance with claim 8, wherein at least one of said stitch-lines is located to permit formation of an open crotch area in said dressing.

11. A dressing in accordance with claim 8, wherein at least one of said stitch-lines is located to permit at least partial longitudinal severing of said dressing.

12. A dressing in accordance with claim 8, wherein at least some of said stitch-lines are located to permit shaping of arm and neck holes in said dressing.

13. *A surgical dressing adjustable for size and shape, comprising a flexible, non-adhering, fluid-permeable inner lining; a mass of fluid-absorbing material superposed congruently with said inner lining; first means for fastening said inner lining and said mass together about their congruent peripheries; and second means for fastening said mass of fluid-absorbing material together along a plurality of preselected lines, said second means being adapted to maintain the structural integrity of said mass when a severing cut is made through said dressing adjacent to one of said preselected lines, said preselected lines being positioned to permit selective adjustment of the size and shape of said dressing by cutting.*

14. *A surgical dressing adjustable for size and shape, comprising a non-adhering porous inner lining roughly shaped to be conformably wrapped about a human trunk; a mass of absorbent material superposed congruently with said inner lining; a protective outer lining superposed congruently with said mass; means for fastening said linings and said mass together about their congruent peripheries; and a plurality of spaced fastening lines through said mass and said outer lining, at least one of said fastening lines being located to permit adjustment of the length of said dressing.*

References Cited

The following references, cited by the Examiner, are of record in the patented file of this patent or the original patent.

UNITED STATES PATENTS

| | | | |
|---|---|---|---|
| 3,343,537 | 9/1967 | Graham | 128—156 |
| 3,441,021 | 4/1969 | Ewdres | 128—156 |
| 3,346,208 | 5/1969 | Fukuda | 128—156 |
| 3,448,595 | 6/1969 | Baltzer et al. | 66—193 |

LAWRENCE W. TRAPP, Primary Examiner

U.S. Cl. X.R.

128—157, 284